US010793500B2

(12) United States Patent
Jouanneau et al.

(10) Patent No.: US 10,793,500 B2
(45) Date of Patent: *Oct. 6, 2020

(54) DISSOCIATION OF 1,4-BIS(4-PHENOXYBENZOYL)BENZENE—LEWIS ACID COMPLEX IN A PROTIC SOLVENT

(71) Applicant: Arkema France, Colombes (FR)

(72) Inventors: Julien Jouanneau, King of Prussia, PA (US); Guillaume Le, Hérouville-Saint-Clair (FR); Steven Schon, King of Prussia, PA (US); John Richardson, King of Prussia, PA (US); Guillaume Vincent, Caen (FR); Jérôme Amstutz, Charly (FR)

(73) Assignee: ARKEMA FRANCE, Colombes (FR)

( * ) Notice: Subject to any disclaimer, the term of this patent is extended or adjusted under 35 U.S.C. 154(b) by 28 days.

This patent is subject to a terminal disclaimer.

(21) Appl. No.: 16/186,039

(22) Filed: Nov. 9, 2018

(65) Prior Publication Data

US 2019/0077739 A1    Mar. 14, 2019

Related U.S. Application Data

(63) Continuation-in-part of application No. 15/981,284, filed on May 16, 2018, now Pat. No. 10,618,863, and a continuation-in-part of application No. 15/981,439, filed on May 16, 2018, now Pat. No. 10,428,002, and a continuation-in-part of application No. 15/981,498, filed on May 16, 2018, now Pat. No. 10,611,715, and a continuation-in-part of application No. 15/982,625, filed on May 17, 2018, and a continuation-in-part of application No. 15/982,453, filed on May 17, 2018, and a continuation-in-part of application No. 15/982,549, filed on May 17, 2018, now Pat. No. 10,344,125.

(30) Foreign Application Priority Data

May 16, 2017  (EP) .................... 17305559
May 16, 2017  (EP) .................... 17305561
May 16, 2017  (EP) .................... 17305562
May 18, 2017  (EP) .................... 17305581
May 18, 2017  (EP) .................... 17305582
May 18, 2017  (EP) .................... 17305583

(51) Int. Cl.
| *C07C 45/46* | (2006.01) |
|---|---|
| *C07C 45/80* | (2006.01) |
| *C08G 65/40* | (2006.01) |
| *C08G 61/12* | (2006.01) |
| *C07C 45/81* | (2006.01) |
| *C07C 45/85* | (2006.01) |

(52) U.S. Cl.
CPC ............. *C07C 45/46* (2013.01); *C07C 45/80* (2013.01); *C07C 45/81* (2013.01); *C07C 45/85* (2013.01); *C08G 61/127* (2013.01); *C08G 65/4012* (2013.01); *C08G 65/4093* (2013.01); C08G 2261/3442 (2013.01); C08G 2261/45 (2013.01); C08G 2650/62 (2013.01)

(58) Field of Classification Search
USPC ...................................................... 528/176
See application file for complete search history.

(56) References Cited

U.S. PATENT DOCUMENTS

| 4,704,448 A | 11/1987 | Brugel |
|---|---|---|
| 4,709,007 A | 11/1987 | Jansons et al. |
| 4,716,211 A | 12/1987 | Clendinning et al. |
| 4,794,155 A | 12/1988 | Woo et al. |
| 4,816,556 A | 3/1989 | Gay et al. |
| 4,826,947 A | 5/1989 | Jansons et al. |
| 4,827,041 A | 5/1989 | Ford et al. |

(Continued)

FOREIGN PATENT DOCUMENTS

| EP | 0 192 260 A1 | 8/1986 |
|---|---|---|
| EP | 0 268 112 A2 | 5/1988 |
| EP | 0 298 771 A2 | 1/1989 |
| EP | 0 316 133 A2 | 5/1989 |
| EP | 0 268 112 A3 | 11/1989 |
| EP | 3 438 085 A1 | 2/2019 |
| GB | 2 287 031 A | 9/1995 |
| IN | 193687 B | 7/2004 |
| SU | 445 643 A | 12/1975 |
| WO | 95/23821 A1 | 9/1995 |

OTHER PUBLICATIONS

U.S. Appl. No. 15/981,284, Jouanneau et al.
U.S. Appl. No. 15/981,439, Jouanneau et al.
U.S. Appl. No. 15/981,498, Jouanneau et al.
U.S. Appl. No. 15/982,625, Le et al.
U.S. Appl. No. 15/982,453, Jouanneau et al.
U.S. Appl. No. 15/982,549, Le et al.
Database WPI Week 197630, Thomson Scientific, AN 1976-57263X, Dec. 19, 1975, XP002775200.
Banihashemi, Ahmad, et al., "New heat stable polyethers, polyketones and polysulfones", *Macromolecular Chemistry and Physics*, vol. 200, No. 10, Oct. 1, 1999, pp. 2284-2293, Wiley-VCH Verlag GmbH, Weinheim, DE (XP055420800).

(Continued)

*Primary Examiner* — Terressa Boykin (74) *Attorney, Agent, or Firm* — Buchanan Ingersoll & Rooney P.C.

(57) ABSTRACT

A method for manufacturing 1,4-bis(4-phenoxybenzoyl)benzene, including: reacting terephthaloyl chloride with diphenyl ether in the presence of a Lewis acid, so as to obtain a product mixture including 1,4-bis(4-phenoxybenzoyl)benzene-Lewis acid complex, wherein the 1,4-bis(4-phenoxybenzoyl)benzene-Lewis acid complex is, at least partly, in the form of a precipitate; carrying out a solid/liquid separation of the product mixture to obtain a cake comprising the 1,4-bis(4-phenoxybenzoyl)benzene-Lewis acid complex precipitate; putting the cake in contact with a decomplexing solvent, wherein the decomplexing solvent is a protic solvent, so as to dissociate the 1,4-bis(4-phenoxybenzoyl)benzene-Lewis acid complex into 1,4-bis(4-phenoxybenzoyl)benzene; and, recovering the 1,4-bis(4-phenoxybenzoyl)benzene. Also, a method for manufacturing a polyaryletherketone polymer starting from 1,4-bis(4-phenoxybenzoyl)benzene manufactured by the above method.

17 Claims, 1 Drawing Sheet

(56) References Cited

U.S. PATENT DOCUMENTS

| | | | |
|---|---|---|---|
| 4,891,167 | A | 1/1990 | Clendinning et al. |
| 4,918,237 | A | 4/1990 | Corbin et al. |
| 4,931,530 | A | 6/1990 | Fukawa et al. |
| 5,137,988 | A | 8/1992 | Matzner et al. |
| 5,258,491 | A | 11/1993 | Agreda et al. |
| 5,734,005 | A | 3/1998 | Daniels et al. |
| 10,344,125 | B2 | 7/2019 | Le et al. |
| 10,428,002 | B2* | 10/2019 | Jouanneau ............... C07C 45/46 |
| 10,611,715 | B2 | 4/2020 | Jouanneau et al. |
| 10,618,863 | B2 | 4/2020 | Jouanneau et al. |
| 2015/0183918 | A1 | 7/2015 | Le et al. |
| 2018/0334418 | A1* | 11/2018 | Jouanneau ............ C08G 61/127 |
| 2018/0334419 | A1* | 11/2018 | Jouanneau ......... C08G 65/4012 |
| 2018/0334420 | A1 | 11/2018 | Le et al. |
| 2018/0334538 | A1 | 11/2018 | Le et al. |
| 2019/0040189 | A1 | 2/2019 | Le et al. |
| 2019/0135721 | A1 | 5/2019 | Jouanneau et al. |
| 2019/0152886 | A1* | 5/2019 | Jouanneau ............... C08L 65/00 |
| 2020/0062683 | A1 | 2/2020 | Jouanneau et al. |
| 2020/0079717 | A1 | 3/2020 | Le et al. |
| 2020/0087456 | A1 | 3/2020 | Le et al. |
| 2020/0109100 | A1 | 4/2020 | Jouanneau et al. |

OTHER PUBLICATIONS

Baysec, Sebnem, et al., "Very High Solid State Photoluminescence Quantum Yields of Poly(tetraphenylethylene) Derivatives", *Macromolecular Rapid Communications*, vol. 37, No. 22, Sep. 26, 2016, pp. 1802-1806, Wiley-VCH Verlag GmbH & Co. KGaA, Weinheim, DE (XP055420789).

Fukawa, Isaburo, et al., "Preparation of Dibenzofuran-Type Amorphous Polyetherketone by Novel Etherification Reaction", *Journal of Polymer Science: Part A: Polymer Chemistry*, 1992, pp. 1977-1985, vol. 30 (XP055420842).

March, Jerry, "Advanced Organic Chemistry", Dec. 31, 1985, p. 333, copyright page, John Wiley & Sons, New York (XP002775202).

Mithyantha, et al., "A process for the purification of 1,4-bis(4-phenoxybenzoyl)benzene", Database Caplus [Online], Aug. 23, 2006, 1 page, Chemical Abstracts Service, Columbus, OH (XP002775201).

Streitwieser, Andrew, et al., "Introduction to Organic Chemistry", Dec. 31, 1981, p. 544, copyright page, Macmillan Publishing Co., Inc., New York (XP002775203).

European Search Report in application No. EP 17305559.1, dated Nov. 9, 2017, European Patent Office, Munich, DE, 10 pages.

European Search Report in application No. EP 17305561.7, dated Nov. 3, 2017, European Patent Office, Munich, DE, 5 pages.

European Search Report in application No. EP 17305562.5, dated Dec. 6, 2017, European Patent Office, Munich, DE, 10 pages.

European Search Report in application No. EP 17305581.5, dated Nov. 24, 2017, European Patent Office, Munich, DE, 6 pages.

European Search Report in application No. EP 17305582.3, dated Nov. 8, 2017, European Patent Office, Munich, DE, 7 pages.

European Search Report in application No. EP 17305583.1, dated Aug. 22, 2017, European Patent Office, Munich, DE, 8 pages.

Jouanneau, Julien M., et al., U.S. Appl. No. 15/981,284 entitled "Method for Manufacturing 1,4-Bis(4-Phenoxybenzoyl) Benzene at an Elevated Temperature," filed May 16, 2018.

Jouanneau, Julien M., et al., U.S. Appl. No. 15/981,439 entitled "Method for Manufacturing 1,4-Bis(4-Phenoxybenzoyl) Benzene in Supersaturation Conditions," filed May 16, 2018.

Jouanneau, Julien, et al., U.S. Appl. No. 15/981,498 entitled "Method for Manufacturing 1,4-Bis(4-Phenoxybenzoyl) Benzene Using Substantially Non-Hydrolyzed Terephthaloyl Chloride," filed May 16, 2018.

Le, Guillaume, et al., U.S. Appl. No. 15/982,625 entitled "Dissociation of a 1,4-Bis(4-Phenoxybenzoyl)Benzene-Lewis Acid Complex in an Aqueous Solution," filed May 17, 2018.

Jouanneau, Julien, et al., U.S. Appl. No. 15/982,453 entitled "Ripening of 1,4-Bis(4-Phenoxybenzoyl)Benzene," filed May 17, 2018.

Le, Guillaume, et al., U.S. Appl. No. 15/982,549 entitled "Purification of 1,4-Bis(4-Phenoxybenzoyl)Benzene by Centrifugal Filtration," filed May 17, 2018.

Brown, R. R., et al., "Solubility and Activity of Aluminum Chloride in Aqueous Hydrochloric Acid Solutions," *RI 8379—Bureau of Mines Report of Investigations/1979*, 1979, United States Department of the Interior, Reproduced by National Technical Information Service, U.S. Department of Commerce, Springfield, VA 22161, 26 pages.

European Search Report in application No. EP 18306473.2, dated Apr. 18, 2019, European Patent Office, Munich, DE, 5 pages.

U.S. Appl. No. 16/609,648, Julien Jouanneau, Guillaume Le and Jérôme Amstutz, filed Oct. 30, 2019.

U.S. Appl. No. 16/609,790, Guillaume Le, Guillaume Vincent and Julien Jouanneau, filed Oct. 31, 2019.

U.S. Appl. No. 16/613,587, Guillaume Le and Julien Jouanneau, filed Nov. 14, 2019.

U.S. Appl. No. 16/613,600, Julien Jouanneau and Guillaume Le, filed Nov. 14, 2019.

U.S. Appl. No. 16/613,454, Julien Jouanneau, Jérôme Amstutz and Guillaume Vincent, filed Nov. 14, 2019.

U.S. Appl. No. 16/613,456, Guillaume Le, Julien Jouanneau and Jérôme Amstutz, filed Nov. 14, 2019.

U.S. Appl. No. 16/609,648, Jouanneau et al.

U.S. Appl. No. 16/609,790, Le et al.

U.S. Appl. No. 16/609,587, Le et al.

U.S. Appl. No. 16/613,600, Jouanneau et al.

U.S. Appl. No. 16/613,454, Jouanneau et al.

U.S. Appl. No. 16/613,456, Le et al.

Jouanneau, Julien, et al., U.S. Appl. No. 16/609,648 entitled "Method for Manufacturing 1,4-Bis(4-Phenoxybenzoyl)Benzene at an Elevated Temperature," filed Oct. 30, 2019.

Le, Guillaume, et al., U.S. Appl. No. 16/609,790 entitled "Method for Manufacturing 1,4-Bis(4-Phenoxybenzoyl)Benzene in Supersaturation Conditions," filed Oct. 31, 2019.

Le, Guillaume, et al., U.S. Appl. No. 16/613,587 entitled "Method for Manufacturing 1,4-Bis(4-Phenoxybenzoyl)Benzene Using Substantially Non-Hydrolyzed Terephthaloyl Chloride," filed Nov. 14, 2019.

Jouanneau, Julien, et al., U.S. Appl. No. 16/613,600 entitled "Dissociation of a 1,4-Bis(4-Phenoxybenzoyl)Benzene-Lewis Acid Complex in an Aqueous Solution," filed Nov. 14, 2019.

Jouanneau, Julien, et al., U.S. Appl. No. 16/613,454 entitled "Ripening of 1,4-Bis(4-Phenoxybenzoyl)Benzene," filed Nov. 14, 2019.

Le, Guillaume, et al., U.S. Appl. No. 16/613,456 entitled "Purification of 1,4-Bis(4-Phenoxybenzoyl)Benzene by Centrifugal Filtration," filed Nov. 14, 2019.

U.S. Appl. No. 15/981,284, Julien M Jouanneau, Guillaume Le and Jérôme Amstutz, filed May 16, 2018, (Cited herein as US Patent Application Publication No. 2018/0334418 A1 of Nov. 22, 2018).

U.S. Appl. No. 15/981,439, Julien M Jouanneau, Guillaume Le and Guillaume Vincent, filed May 16, 2018, (Cited herein as US Patent Application Publication No. 2019/0135721 A1 of May 9, 2019).

U.S. Appl. No. 15/981,498, Julien M Jouanneau and Guillaume Le, filed May 16, 2018, (Cited herein as US Patent Application Publication No. 2018/0334419 A1 of Nov. 22, 2018).

U.S. Appl. No. 15/982,625, Guillaume Le and Julien Jouanneau, filed May 17, 2018, (Cited herein as US Patent Application Publication No. 2018/0334420 A1 of Nov. 22, 2018).

U.S. Appl. No. 15/982,453, Julien Jouanneau, Jérôme Amstutz and Guillaume Vincent, filed May 17, 2018, (Cited herein as US Patent Application Publication No. 2019/0152886 A1 of May 23, 2018).

International Search Report and Written Opinion, issued in PCT/EP2018/062803, dated Jul. 12, 2018, European Patent Office, Rijswijk, NL, 10 pages.

International Search Report and Written Opinion, issued in PCT/EP2018/062796, dated Aug. 20, 2018, European Patent Office, Rijswijk, NL, 7 pages.

International Search Report and Written Opinion, issued in PCT/EP2018/062813, dated Jun. 29, 2018, European Patent Office, Rijswijk, NL, 11 pages.

(56) References Cited

OTHER PUBLICATIONS

International Search Report and Written Opinion, issued in PCT/EP2018/063013, dated Jul. 24, 2018, European Patent Office, Rijswijk, NL, 8 pages.

International Search Report and Written Opinion, issued in PCT/EP2018/063017, dated Jul. 4, 2018, European Patent Office, Rijswijk, NL, 9 pages.

International Search Report and Written Opinion, issued in PCT/EP2018/063014, dated Jul. 24, 2018, European Patent Office, Rijswijk, NL, 10 pages.

International Search Report and Written Opinion issued in PCT/EP2019/080625, dated Jan. 20, 2020, European Patent Office, Rijswijk, NL, 7 pages.

Stevens, G.W., et al., "Extraction, Liquid-Liquid," *Kirk-Othmer Encyclopedia of Chemical Technology*, 2007, pp. 1-62, John Wiley & Sons, Inc., NJ, United States (published online Jun. 15, 2007).

\* cited by examiner

DISSOCIATION OF 1,4-BIS(4-PHENOXYBENZOYL)BENZENE—LEWIS ACID COMPLEX IN A PROTIC SOLVENT

CROSS REFERENCE TO RELATED APPLICATIONS

The present application is:

a continuation in part of U.S. application Ser. No. 15/981,284, filed on May 16, 2018, now U.S. Pat. No. 10,618,863, which claims the benefit of European Application No. 17305559, filed on May 16, 2017;

a continuation in part of U.S. application Ser. No. 15/981,439, filed on May 16, 2018, now U.S. Pat. No. 10,428,002, which claims the benefit of European Application No. 17305561, filed on May 16, 2017;

a continuation in part of U.S. application Ser. No. 15/981,498, filed on May 16, 2018, now U.S. Pat. No. 10,611,498, which claims the benefit of European Application No. 17305562, filed on May 16, 2017;

a continuation in part of U.S. application Ser. No. 15/982,625, filed on May 17, 2018, which claims the benefit of European Application No. 17305581, filed on May 18, 2017;

a continuation in part of U.S. application Ser. No. 15/982,453, filed on May 17, 2018, which claims the benefit of European Application No. 17305582, filed on May 18, 2017; and a continuation in part of U.S. application Ser. No. 15/982,549, filed on May 17, 2018, now U.S. Pat. No. 10,344,125, which claims the benefit of European Application No. 17305583, filed on May 18, 2017.

The entire contents of each of U.S. application Ser. No. 15/981,284, European Application No. 17305559, U.S. application Ser. No. 15/981,439, European Application No. 17305561, U.S. application Ser. No. 15/981,498, European Application No. 17305562, U.S. application Ser. No. 15/982,625, European Application No. 17305581, U.S. application Ser. No. 15/982,453, European Application No. 17305582, U.S. application Ser. No. 15/982,549, European Application No. 17305583 are hereby incorporated herein by reference in their entirety.

TECHNICAL FIELD

The present application relates to a method for manufacturing 1,4-bis(4-phenoxybenzoyl)benzene, as well as a method for manufacturing polyaryl ether ketone polymers, in particular polyether ketone ketone polymers, starting from said 1,4-bis(4-phenoxybenzoyl)benzene.

TECHNICAL BACKGROUND

Polyether ketone ketone (PEKK) polymers have a number of properties which make them useful for applications involving exposure to high temperature or to high mechanical or chemical stress. They are for instance useful in the aerospace industry, in off-shore drilling and in medical devices.

One known route for manufacturing polyether ketone ketone polymers relies on the use of 1,4-bis(4-phenoxybenzoyl)benzene as a starting material.

1,4-bis(4-phenoxybenzoyl)benzene can be prepared by reacting terephthaloyl chloride and diphenyl ether in the presence of a Lewis acid such as aluminum trichloride.

In document U.S. Pat. No. 4,816,556 (example 2), 1,4-bis(4-phenoxybenzoyl)benzene is prepared by dissolving terephthaloyl chloride and diphenyl ether in ortho-dichlorobenzene and adding aluminum chloride. Thereafter, cold methanol is added so as to produce a slurry which is filtered, reslurried in methanol and filtered again.

In document U.S. Pat. No. 4,826,947 (example 2), 1,4-bis(4-phenoxybenzoyl)benzene is prepared by providing a mixture of methylene chloride, methylsulfone and aluminum trichloride, adding diphenyl ether and thereafter terephthaloyl chloride. The reaction mixture is then poured into cold methanol so as to make a slurry which is then filtered.

Document WO 95/23821 (example 11) discloses providing aluminum chloride in ortho-dichlorobenzene and then adding terephthaloyl chloride and diphenyl ether. Thereafter, the reaction mixture is allowed to warm up to room temperature, stirred, and poured into a methanol concentrated HCl solution. A precipitate is formed which is subsequently filtered off.

There is still a need for a method for manufacturing 1,4-bis(4-phenoxybenzoyl)benzene with a high purity and a high yield, which can be implemented at the industrial scale in an economically realistic manner.

SUMMARY

It is a first object of the invention to provide a method for manufacturing 1,4-bis(4-phenoxybenzoyl)benzene, comprising:

reacting terephthaloyl chloride with diphenyl ether in the presence of a Lewis acid, so as to obtain a product mixture comprising 1,4-bis(4-phenoxybenzoyl)benzene-Lewis acid complex, wherein the 1,4-bis(4-phenoxybenzoyl)benzene-Lewis acid complex is, at least partly, in the form of a precipitate;

carrying out a solid/liquid separation of the product mixture to obtain a cake comprising the 1,4-bis(4-phenoxybenzoyl)benzene-Lewis acid complex precipitate;

putting the cake in contact with a decomplexing solvent, wherein the decomplexing solvent is a protic solvent, so as to dissociate the 1,4-bis(4-phenoxybenzoyl)benzene-Lewis acid complex into 1,4-bis(4-phenoxybenzoyl)benzene; and recovering the 1,4-bis(4-phenoxybenzoyl)benzene.

The inventors have shown that it is advantageous to carry out a solid/liquid separation of the product/mixture to obtain a cake containing the 1,4-bis(4-phenoxybenzoyl)benzene-Lewis acid complex precipitate and to subsequently dissociate the 1,4-bis(4-phenoxybenzoyl)benzene-Lewis acid complex contained in the cake by putting it in contact with a decomplexing solvent, in order to obtain 1,4-bis(4-phenoxybenzoyl)benzene with a high yield and a high purity. In particular, the recovered 1,4-bis(4-phenoxybenzoyl)benzene has a very low content of impurities such as xanthydrol moiety-containing molecules. In some preferred embodiments, the content of xanthydrol moiety-containing molecules in the recovered 1,4-bis(4-phenoxybenzoyl)benzene is less than 1 wt. %.

Carrying out an extraction by solid/liquid separation on the 1,4-bis(4-phenoxybenzoyl)benzene-Lewis acid complex precipitate, prior to the step of dissociation into 1,4-bis(4-phenoxybenzoyl)benzene offers at least two advantages compared to the reverse operation. Firstly, the 1,4-bis(4-phenoxybenzoyl)benzene-Lewis acid complex precipitate has a higher density than 1,4-bis(4-phenoxybenzoyl)benzene and can therefore be extracted more easily by solid/liquid separation means than 1,4-bis(4-phenoxybenzoyl)benzene. Secondly, soluble impurities, such as xanthydrol moiety-containing molecules, are mostly eliminated in the liquid phase during the solid/liquid separation of the product mixture, so that the 1,4-bis(4-phenoxybenzoyl)benzene-Lewis acid complex precipitate, and therefore the recovered 1,4-bis(4-phenoxybenzoyl)benzene, is substantially free from soluble impurities in the liquid phase.

In some embodiments, reacting terephthaloyl chloride with diphenyl ether in the presence of a Lewis acid is carried out in a reaction solvent, wherein the reaction solvent is separate from the terephthaloyl chloride, the diphenyl ether, and the Lewis acid. In these embodiments, the reaction solvent is preferably non-protic. More preferably, the reaction solvent is selected from the group consisting of: methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof. Even more preferably, the reaction solvent is ortho-dichlorobenzene.

In some embodiments, the 1,4-bis(4-phenoxybenzoyl) benzene-Lewis acid complex precipitate has a volumetric mass density between 1.34 kg/m$^3$ and 2.40 kg/m$^3$, measured by a pycnometer at 23° C. The higher the volumetric mass density of 1,4-bis(4-phenoxybenzoyl)benzene-Lewis acid complex precipitate is, the easier it is to separate it from liquid by solid/liquid extraction. In particular, the 1,4-bis(4-phenoxybenzoyl)benzene-Lewis acid complex precipitate has often a volumetric mass density between 1.50 kg/m$^3$ and 2.20 kg/m$^3$. In particular, the volumetric mass density of 1,4-bis(4-phenoxybenzoyl)benzene-Lewis acid complex precipitate can be between 1.60 kg/m$^3$ and 2.00 kg/m$^3$.

In some embodiments, the cake has a solid content of at least 40 wt. %. The higher the solid content of the cake is, the more soluble impurities are eliminated with the liquid phase during the solid/liquid separation. Therefore, the cake has preferably a solid content of at least 50 wt. %, or at least 60 wt. %, or at least 70 wt. %, or at least 75 wt. %, or at least 80 wt. %, or at least 85 wt. %, or at least 90 wt. %, or at least 95 wt. %. More preferably, the cake has a solid content of about 100 wt. %.

In some embodiments, the decomplexing solvent is a protic solvent chosen from the group consisting of: methanol, acetic acid, formic acid, ethanol, isopropanol, benzyl alcohol, aqueous solutions and mixtures thereof.

In some embodiments, the decomplexing solvent is an aqueous solution.

In some embodiments, the decomplexing solvent has a pH of no more than 6, or no more than 5, or no more than 4, or no more than 3, or no more than 2, or no more than 1, or no more than 0. Preferably, the decomplexing solvent has a pH between 1 and 2.

In some other embodiments, the decomplexing solvent has a pH of more than 9, or more than 10, or more than 11, or more than 12, or more than 13. Preferably, the decomplexing solvent has a pH between 12 and 14.

In some embodiments, the temperature when carrying out the solid/liquid separation of the product mixture does not exceed 79° C. Preferably, the temperature when carrying out the solid/liquid separation of the product mixture does not exceed 60° C. More preferably, the temperature when carrying out the solid/liquid separation of the product mixture does not exceed 30° C.

In some embodiments, solid/liquid separation is carried out in one or more successive steps, each step being chosen from the group consisting of: centrifugal filtration, sedimentation, centrifugal decanting, filtration under vacuum, filtration under pressure, and gravity filtration.

In some embodiments, the Lewis acid is selected from the group consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Preferably, the Lewis acid is selected from the group consisting of: aluminum trichloride, boron trichloride, aluminum tribromide, titanium tetrachloride, antimony pentachloride, ferric chloride, gallium trichloride, and molybdenum pentachloride. More preferably, the Lewis acid is aluminum trichloride.

In some embodiments, the product mixture is cooled down and/or submitted to shear stress and/or submitted to the removal by distillation of part of the reaction solvent, and/or subject to the addition of a compound in solid form acting as a seed in order to foster the 1,4-bis(4-phenoxybenzoyl)benzene-Lewis acid complex precipitation.

In some embodiments, reacting terephthaloyl chloride with diphenyl ether in the presence of the Lewis acid is carried out, at least partly, at a temperature greater than 5° C.

In some embodiments, the terephthaloyl chloride is of a purity grade such that, 10 minutes after introducing it at a reference concentration of 6.5 wt. % into said solvent, at a temperature of 20° C., a solution is obtained having a turbidity of less than 500 NTU.

In some embodiments, the 1,4-bis(4-phenoxybenzoyl) benzene-Lewis acid complex is dissolved in the reaction solvent at a 1,4-bis(4-phenoxybenzoyl)benzene weight concentration in the reaction solvent which is higher than the saturation limit of the 1,4-bis(4-phenoxybenzoyl)benzene-Lewis acid complex during at least part of the reaction of the terephthaloyl chloride with the diphenyl ether.

It is a second object of the invention to provide a method of making a polyaryl ether ketone comprising:

manufacturing 1,4-bis(4-phenoxybenzoyl)benzene according to the method of any one of the disclosed embodiments; and reacting said 1,4-bis(4-phenoxybenzoyl)benzene with at least one difunctional aromatic acyl chloride.

DESCRIPTION OF EMBODIMENTS

Embodiments of the invention will now be described in more detail without limitation in the following description.

1,4-bis(4-phenoxybenzoyl)benzene (abbreviated name: EKKE) is the compound of formula I:

(I)

It may be made by reacting terephthaloyl chloride of formula II:

(II)

with diphenyl ether of formula III:

(III)

in a solvent (the reaction solvent), and in the presence of a Lewis acid, acting as a Friedel-Crafts catalyst.

The reaction results in the production of the compound of formula I which is predominantly in the form of a complex with the Lewis acid.

It is believed that the reaction comprises two stages. In the first stage, one molecule of formula II reacts with one molecule of formula III to form the intermediate 4-(4-phenoxybenzoyl)benzoyl chloride of formula IV, which is called an "active intermediate":

(IV)

Then, one molecule of the active intermediate of formula IV reacts with another molecule of formula III to form the desired product of formula I.

During the reaction, 4-(4-phenoxybenzoyl)benzoic acid of formula IVa can also be produced to some extent (notably from the active intermediate of formula IV):

(IVa)

The corresponding 4-(4-phenoxybenzoyl)benzoic acid ester can be formed either directly from the acyl chloride of formula IV or from the carboxylic acid of formula IVa. The acid form and/or the ester form of the intermediate can be formed during the reaction but they can also primarily be formed from the remaining active intermediate during subsequent workup.

The 4-(4-phenoxybenzoyl)benzoic acid and 4-(4-phenoxybenzoyl)benzoic acid ester are inactive and therefore remain as impurities in the product mixture.

The other main impurities produced by the reaction are xanthydrol moiety-containing molecules of formula (V):

(V)

In some embodiments, the terephthaloyl chloride, the diphenyl ether or the Lewis acid can play the role of the reaction solvent.

On the opposite, in other embodiments, the reaction solvent can be a separate solvent from the diphenyl ether, the terephthaloyl chloride, or the Lewis acid. In these embodiments, the reaction solvent is preferably a non-protic solvent. A protic solvent is a solvent containing at least one hydrogen atom bound to an oxygen or nitrogen atom, and which is therefore able to donate protons to reagents. A non-protic solvent is a solvent which is not a protic solvent.

The non-protic solvent used herein can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof.

Ortho-dichlorobenzene is a preferred reaction solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The reaction between the compounds of formulas (II) and (III) to make the compound of formula (I) may be performed in a reactor. The reactor can be for instance a glass reactor, a glass-lined reactor or a stainless-steel reactor.

According to some variations, the materials introduced into the reactor in the method of embodiments of the invention consist essentially, or consist, of the compounds of formulas (II) and (III), the reaction solvent and the Lewis acid.

In one embodiment, as a first step, a starting mixture comprising (and preferably consisting of) terephthaloyl chloride and diphenyl ether in the reaction solvent is provided. The starting mixture can be made by mixing the three components together, in any order. By way of example, the reaction solvent can be introduced first in the reactor, and then the two reactants can be added to the reactor. As a second step, the last chemical to be added, i.e. the Lewis acid, is added to the starting mixture. Preferably, the Lewis acid is added as a solid. Alternatively, it can also be added as a suspension or a colloid, namely as a heterogeneous mixture of solid particles of Lewis acid in a solvent. The solvent for the suspension/colloid is advantageously the abovementioned reaction solvent. Alternatively, it can also be added as a solution, namely as a homogeneous mixture of Lewis acid in a solvent. The solvent for the solution is preferably the abovementioned reaction solvent. In some variations, the Lewis acid is added in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving.

In a second embodiment, as a first step, a starting mixture comprising (and preferably consisting of) terephthaloyl chloride and the Lewis acid in the reaction solvent is provided. The starting mixture can be made by mixing the three components together, in any order. As a second step, the diphenyl ether is added to the starting mixture. The diphenyl ether can be added in its liquid form or as a solution, preferably in the abovementioned reaction solvent.

In a third embodiment, as a first step, a starting mixture comprising (and preferably consisting of) diphenyl ether and the Lewis acid in the reaction solvent is provided. The starting mixture can be made by mixing the three components together, in any order. As a second step, the terephthaloyl chloride is added to the starting mixture. The terephthaloyl chloride can be added as a solid or as a liquid. Alternatively, it can be added as a suspension or as a colloid, or a solution, preferably in the abovementioned reaction solvent.

In some variations of the second embodiment and third embodiment, part of the Lewis acid can be included in the starting mixture at the first step, and part of the Lewis acid can be added to the starting mixture at the second step. For example, in the second embodiment, as the second step, a mixture of diphenyl ether and Lewis acid may be added to the starting mixture. For example, in the third embodiments, as the second step, a mixture of terephthaloyl chloride and Lewis acid may be added to the starting mixture.

In some embodiments, the compound of formula II used as a starting material is provided with a high purity grade. Hydrolyzed forms of the compound of formula II are difficult to analyze and quantify in the starting material. It has been found that one practical method to ensure that the compound of formula II has the requisite purity is to dissolve it in a solvent, and to analyze its turbidity. It has been found that a high turbidity value in this test (which is indicative of a significant amount of insoluble contaminants within the starting material) results in a poor yield and a high amount of undesirable by-products in the manufacture of the compound of formula I.

Accordingly, the compound of formula II is preferably of a purity grade such that, 10 minutes after introducing it at a reference concentration of 6.5 wt. % in the solvent, at a temperature of 20° C., a solution is obtained having a turbidity of less than 500 NTU. Turbidity values are provided relative to a sample of solvent without compound of formula II.

In some embodiments, the solvent used in the turbidity test can be the same solvent as the reaction solvent. On the contrary, in other embodiments, the solvent used in the turbidity test can be a different solvent than the reaction solvent.

Preferably, the turbidity is less than 200 NTU, more preferably less than 100 NTU, even more preferably less than 50 NTU and most preferably less than 10 NTU.

A more stringent test consists in waiting for 10 hours, or even for 24 hours, between the introduction of the compound of formula II into the solvent and the turbidity measurement. Preferably, turbidity values of less than 500 NTU, preferably less than 200 NTU, more preferably less than 100 NTU, even more preferably less than 50 NTU and most preferably less than 10 NTU are obtained in this more stringent test.

In some variations, a second turbidity value may be obtained with a sample of solvent of so-called anhydrous grade; which is stored on a molecular sieve. Preferably, the anhydrous grade of solvent is characterized by a water weight content of less than 50 ppm, preferably of less than 30 ppm. In embodiments, the second, anhydrous turbidity value may be less than 500 NTU, preferably less than 200 NTU, more preferably less than 100 NTU, even more preferably less than 50 NTU and most preferably less than 10 NTU.

In other variations, the turbidity values indicated herein are obtained using a sample of the batch of solvent which is used for the reaction itself. This is particularly advantageous for the turbidity measurements conducted 10 hours or 24 hours after the introduction of the compound into the reaction solvent, since the measurement is then representative of the actual quality of the compound in the reaction conditions, depending also on the quality of the solvent.

In a particular embodiment, the solvent used for the turbidity test is ortho-dichlorobenzene containing less than 100 ppm by weight of water. The turbidity may be assessed by introducing 1580 mg of terephthaloyl chloride into 22.6 g of ortho-dichlorobenzene containing less than 100 ppm by weight of water in a 50 mL flask, and by agitating the mixture with a magnetic stirrer, under nitrogen atmosphere. After 10 minutes, the turbidity of the mixture may be measured on a 20 mL sample with a Hach Lange Turbidimeter, using the same solvent as a blank sample.

The ortho-dichlorobenzene used for the turbidity test can have a content by weight of water of from 50 to 75 ppm; or from 75 to 100 ppm. The ortho-dichlorobenzene used for the turbidity test can also have a content by weight of water less than 50 ppm, in particular from 1 to 5 ppm; or from 5 to 10 ppm; or from 10 to 20 ppm; or from 20 to 30 ppm; or from 30 to 40 ppm; or from 40 to 50 ppm.

A number of steps can be taken in order to ensure that the compound of formula II is of a satisfactory purity grade. In particular, the compound should substantially not be in contact with water at any time before the reaction. It can thus be advantageous to keep this material in a sealed container without contact with ambient air. Keeping the material in a nitrogen atmosphere may in particular be useful.

As a sealed container, use may in particular be made of a container having walls and a lid having a moisture vapor transmission rate of not more than 0.1 $g/m^2$. 24 h at a relative humidity of 90% and a temperature of 37.8° C.

The container walls may be for instance made of polyethylene, such as high-density polyethylene.

The container walls may preferably have a thickness of at least 0.5 mm, more preferably at least 1 mm.

In some embodiments, the reaction solvent and the compound of formula III used for the reaction can also have a low water content.

Accordingly, the reaction solvent preferably contains less than 500 ppm by weight of water, advantageously less than 250 ppm by weight of water, preferably less than 150 ppm by weight of water, more preferably less than 100 ppm by weight of water, and most preferably less than 50 ppm by weight of water. In preferred variations, the above weight ranges also apply in a similar manner to the compound of formula III and the reaction solvent in combination.

Possible weight ranges of water content in the reaction solvent are: from 1 to 5 ppm; or from 5 to 10 ppm; or from 10 to 20 ppm; or from 20 to 30 ppm; or from 30 to 40 ppm; or from 40 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 500 ppm. Ranges of from 1 to 250 ppm, or from 2 to 200 ppm, or from 3 to 150 ppm, or from 4 to 100 ppm, or from 5 to 50 ppm are particularly preferred. In preferred variations, the above weight ranges also apply in a similar manner to the compound of formula III and the reaction solvent in combination.

A number of steps can be taken in order to ensure that the compound of formula III and/or the reaction solvent do not contain an excessive amount of water. In particular, it is desirable to keep these materials in sealed containers without contact with ambient air. Keeping the materials in a dry nitrogen atmosphere may in particular be useful.

In some variations, the method of the invention comprises a preliminary step of drying, i.e., reducing the water content, of the reaction solvent and/or the compound of formula III, before use. This step may be performed, e.g., by distillation or by contacting with a molecular sieve or with a dehydrating agent.

By way of example, the weight proportion of water in the solvent, or in the solvent combined with the compound of formula III, may be reduced owing to the drying step from an initial value of 50 to 300 ppm to a final value of less than 100 ppm, preferably less than 50 ppm, more preferably less than 30 ppm.

The Lewis acid used in the method of the invention is preferably of a purity grade such that it comprises less than 0.1 wt. % insoluble matter, and more preferably less than 0.05 wt. % insoluble matter, as measured by gravimetry, when introduced into the solvent at a concentration of 5 wt. % and substantially dissolved under agitation.

In some particular embodiments, the weight concentrations and weight ratios of the reactants and of the catalyst are as follows:
- the concentration of terephthaloyl chloride (relative to the sum of reaction solvent, terephthaloyl chloride, diphenyl ether and Lewis acid introduced into the reactor) is from 3 to 12%, preferably from 5 to 10%;
- the concentration of diphenyl ether (relative to the sum of reactive solvent, terephthaloyl chloride, diphenyl ether and Lewis acid introduced into the reactor) is from 5 to 35%, preferably from 12 to 25%;
- the concentration of Lewis acid (relative to the sum of reactive solvent, terephthaloyl chloride, diphenyl ether and Lewis acid introduced into the reactor) is from 4 to 30%, preferably from 10 to 25%;
- the weight ratio of terephthaloyl chloride to diphenyl ether introduced into the reactor is from 0.2 to 0.6, preferably from 0.3 to 0.5;
- the weight ratio of Lewis acid to terephthaloyl chloride plus diphenyl ether introduced into the reactor is from 0.2 to 0.9, preferably from 0.3 to 0.7.

The addition of the last chemical is preferably performed progressively, over a period of time which can advantageously range from 5 to 600 minutes, preferably from 30 to 300 minutes. In particular, in the embodiment in which the Lewis acid is added last, the addition of the last chemical is preferably performed progressively, over a period of time which can range from 5 to 600 minutes, preferably from 30 to 300 minutes.

The addition of the last chemical can be performed continuously or with one or more interruptions. If it is performed continuously, it can be conducted at a constant rate of addition. Alternatively, the rate of addition of the last chemical can vary over time.

The starting mixture is preferably agitated during at least part of the reaction step. Thus, the reactor is preferably provided with an agitation device such as a mechanical stirrer (which may, e.g., comprise one or more impellers) or a recirculation loop with a pump.

Preferably, the starting mixture may be agitated using the agitation device during the addition of the last chemical.

Once the addition of the last chemical to the starting mixture is complete, the reaction step may optionally comprise a step of maintaining the starting mixture, preferably under agitation, for a certain time, in order to complete the reaction to the desired degree. Preferably, the mixture is maintained from 0 to 600 min, more preferably from 5 to 180 min.

Once the reaction has been completed to the desired degree, the starting mixture becomes designated as a product mixture.

The reaction at stake is exothermic. Preferably, a temperature control system is provided, in order to control the temperature of the starting mixture in the reactor, in particular during and after mixing/adding the Lewis acid to the starting mixture and during and after adding the last chemical to the starting mixture. The temperature control system may in particular comprise a temperature sensor within the reactor and may be configured to cool and/or to heat the starting mixture. Preferably, it is at least configured to cool the starting mixture.

Devices for heating and/or cooling the starting mixture may include a heat exchanger inside the reactor or in a recirculation loop, or a heat exchange fluid circuit in the jacket of the reactor.

When the temperature of the starting mixture increases during the step of adding the last chemical, this can be achieved in three different manners:
- by heating the starting mixture (while preferably also controlling the rate of addition of the last chemical, so as to achieve a targeted increase in temperature);
- by simply controlling the rate of addition of the last chemical so as to achieve a targeted increase in temperature, without providing external cooling or heating; or
- by cooling the starting mixture, while also controlling the rate of addition of the last chemical, so as to achieve a targeted increase in temperature.

According to a preferred embodiment, the starting mixture is cooled during and possibly also after the step of adding the last chemical, in order to prevent an excessively large or rapid increase in temperature of the starting mixture as the reactants start reacting with each other.

Preferably, the temperature of the starting mixture is greater than 5° C. during at least part of the step of adding the last chemical to the starting mixture. In particular variations, the temperature of the starting mixture is at least 10° C., or at least 15° C., or at least 20° C., or at least 25°

C., or at least 30° C., or at least 35° C., or at least 40° C., or at least 45° C., or at least 50° C., or at least 55° C., or at least 60° C., or at least 65° C., or at least 75° C., or at least 85° C., or at least 95° C., or at least 100° C., or at least 110° C., or about 120° C. during at least part of the step of adding the last chemical to the starting mixture.

Conducting the reaction step at a relatively high temperature may result in an increase in the yield of 1,4-bis(4-phenoxybenzoyl)benzene, without any significant increase in the level of by-product impurities such as xanthydrol moiety-containing molecules.

On the other hand, the temperature during the step of adding the last chemical to the starting mixture should preferably remain below a certain threshold in order to avoid any significant polymerization of the reactants into a PEKK polymer.

Furthermore, the temperature during the step of adding the last chemical to the starting mixture should preferably remain below the boiling temperature of the reaction solvent.

It is possible to operate the reactor in a pressurized manner so that the temperature in the reactor can reach a higher value without causing the reaction solvent to boil or without causing a pressure build up no sustainable by conventional equipment. In this case, the pressure in the reactor can range from 1 bar (atmospheric pressure) to 6 bar, preferably from 1.5 bar to 3 bar.

Alternatively, and preferably, the reaction may be performed at atmospheric pressure.

According to some variants, the temperature of the starting mixture does not exceed 180° C., preferably does not exceed 120°, or does not exceed 100° C., or does not exceed 90° C., or does not exceed 80° C., and more preferably does not exceed 70° C., during the step of adding the last chemical.

The temperature of the starting mixture can remain constant during the step of adding the last chemical. Alternatively, it can vary during this step.

In preferred variations, the temperature of the starting mixture increases during the step of adding the last chemical, i.e., the final temperature is greater than the initial temperature.

In some embodiments, the temperature difference ΔT between the final temperature and the initial temperature is from 1 to 120° C., preferably from 1 to 70° C., preferably from 5 to 60° C., more preferably from 10 to 50° C., and even more preferably from 20 to 40° C.

In some variations, the temperature of the starting mixture continuously increases from the initial temperature to the final temperature. Alternatively, the temperature of the starting mixture may comprise one or more increase stages and one or more plateau stages during the step of adding the last chemical. In particular, the temperature of the starting mixture may initially increase during a first part of the step of adding the last chemical, from the initial temperature to the final temperature, and then plateau at the final temperature during a second part of the step of adding the last chemical. In this case, the plateaued temperature may be set with a precision of, e.g., +/−5° C., or +/−2° C., or +/−1° C.

There is no limitation as to the temperature of the starting mixture during the optional step of maintaining the mixture, after the addition of the last chemical. In some variations, the temperature of the mixture is maintained at the final temperature described above. In other variations, it increases or decreases relative to the final temperature.

During the reaction step, 1,4-bis(4-phenoxybenzoyl)benzene-Lewis acid complex is initially produced as a dissolved species, the concentration of which progressively increases.

In preferred embodiments, at some point of time during the reaction step, the concentration of the 1,4-bis(4-phenoxybenzoyl)benzene-Lewis acid complex exceeds the saturation limit of the 1,4-bis(4-phenoxybenzoyl)benzene-Lewis acid complex. In other terms, in these embodiments, the 1,4-bis(4-phenoxybenzoyl)benzene-Lewis acid complex is maintained in a supersaturated state during at least part of the step of reacting terephthaloyl chloride with diphenyl ether.

This saturation limit depends on the conditions of the starting mixture in real time and may vary during the reaction step. It depends on the temperature of the starting mixture, the nature of the reaction solvent and the amount of Lewis-acid.

The 1,4-bis(4-phenoxybenzoyl)benzene-Lewis acid complex is said to be in a supersaturated state when it is dissolved in the starting mixture at a concentration exceeding the saturation limit. The supersaturated state is a metastable state. Therefore, the 1,4-bis(4-phenoxybenzoyl)benzene-Lewis acid complex in a supersaturated state is able to suddenly precipitate if a nucleating agent (e.g., solid particles), such as hydrolyzed terephthaloyl chloride, is present in the starting mixture.

By way of convention, in the present application the concentration of the 1,4-bis(4-phenoxybenzoyl)benzene-Lewis acid complex is indicated by the weight concentration of 1,4-bis(4-phenoxybenzoyl)benzene in the reaction solvent. The same applies to the saturation limit.

The saturation limit can be determined using the following model experiment: predetermined quantities of 1,4-bis(4-phenoxybenzoyl)benzene and Lewis acid are added to a given solvent, being the same as the reaction solvent, contained in a glass tube. The contents of the glass tube are agitated by magnetic stirring. The temperature of the mixture within the tube is controlled by placing the tube in a thermofluid. The initial temperature is such that the 1,4-bis(4-phenoxybenzoyl)benzene-Lewis acid complex is initially present as a suspension in the reaction solvent. Then the temperature is gradually increased until the 1,4-bis(4-phenoxybenzoyl)benzene-Lewis acid complex gets fully solubilized in the reaction solvent. At this particular temperature, the saturation limit is equal to the weight concentration of 1,4-bis(4-phenoxybenzoyl)benzene in the mixture. The experiment can be repeated a number of times using another weight concentration of 1,4-bis(4-phenoxybenzoyl)benzene and the same weight ratio of Lewis acid with respect to 1,4-bis(4-phenoxybenzoyl)benzene, so that a temperature/saturation curve can be finally obtained for a given reaction solvent and a given weight ratio of Lewis acid to 1,4-bis(4-phenoxybenzoyl)benzene.

It has been found by the present inventors that maintaining the 1,4-bis(4-phenoxybenzoyl)benzene-Lewis acid complex in a supersaturated state during part of the reaction step can result in an increased yield or conversion.

Figure 1:
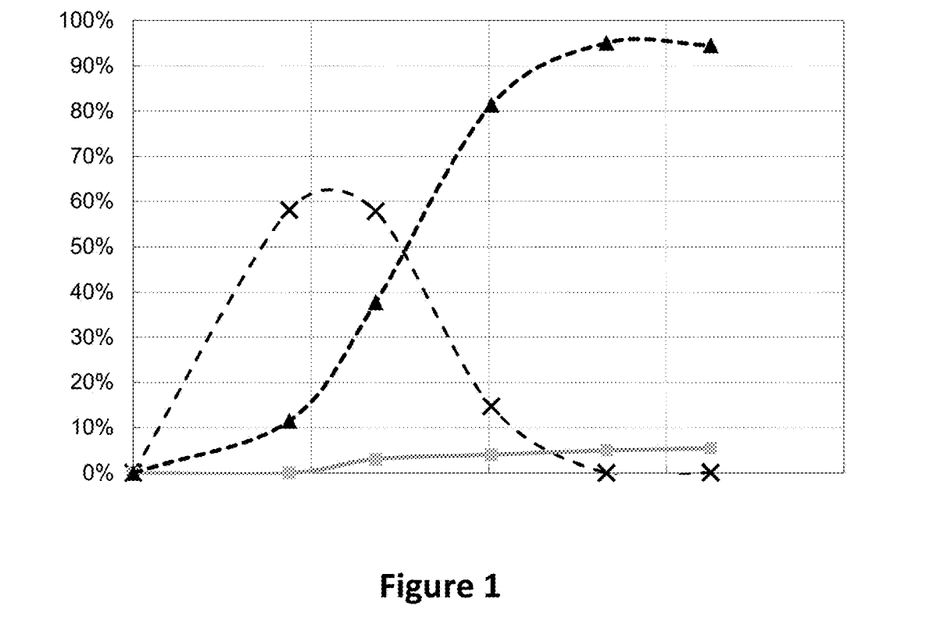
FIG. 1 schematically shows the evolution of the concentration of 4-(4-phenoxybenzoyl)benzoyl chloride (as defined below) (A), 1,4-bis(4-phenoxybenzoyl)benzene (B) and xanthydrol moiety-containing molecules (C), as a function of the progression of the reaction. The concentrations are provided in mol. % relative to the initial total amount of terephthaloyl chloride. The progression of the reaction is indicated in arbitrary units on the X-axis.

The phenomenon at stake is schematically illustrated in FIG. 1, which shows the typical evolution of the concentration of the relevant species in the starting mixture during the reaction step. It can be seen that, the 4-(4-phenoxybenzoyl)benzoyl chloride (A) is initially produced in a large amount. Then the concentration of 4-(4-phenoxybenzoyl)benzoyl chloride in the starting mixture reaches a peak and decreases, while the concentration of the desired product (B)

increases. The amount of xanthydrol moiety-containing impurities (C) increases over time but remains at a relatively low level.

If the 1,4-bis(4-phenoxybenzoyl)benzene-Lewis acid complex precipitates during the reaction step, it is believed (without wishing to be bound by any theory) that part of the unreacted 4-(4-phenoxybenzoyl)benzoyl chloride is caught in the precipitate and thus substantially prevented from further reacting. In other terms, after the 1,4-bis(4-phenoxybenzoyl)benzene-Lewis acid complex has precipitated, it is believed that the conversion of the remaining 4-(4-phenoxybenzoyl)benzoyl chloride (A) to the desired product (B) is significantly impeded.

Therefore, in preferred embodiments, this precipitation is either prevented or at least postponed during the reaction step, without however keeping the concentration of 1,4-bis (4-phenoxybenzoyl)benzene-Lewis acid complex in the mixture at a low level, which would in turn reduce the overall efficiency and kinetics of the reaction. This is made possible because the 1,4-bis(4-phenoxybenzoyl)benzene-Lewis acid complex remains dissolved in the reaction solvent during at least part of the reaction step even after its concentration has reached the saturation limit.

According to some variations, the 1,4-bis(4-phenoxybenzoyl)benzene-Lewis acid complex precipitates at some point of time during the reaction step (after the concentration of this species has exceeded the saturation limit).

According to alternative variations, the 1,4-bis(4-phenoxybenzoyl)benzene-Lewis acid complex does not precipitate during the reaction step and remains dissolved in the reaction solvent during the entirety of the reaction step.

Preferably, the 1,4-bis(4-phenoxybenzoyl)benzene-Lewis acid complex is dissolved in the reaction solvent during at least 75%, or at least 80%, or at least 85%, or at least 90%, or at least 95%, or at least 98%, or at least 99% of the overall duration of the reaction step.

Preferably, the 1,4-bis(4-phenoxybenzoyl)benzene-Lewis acid complex is still dissolved in the reaction solvent (i.e., has not precipitated), when it is present in an amount of 75 mol. %, (or in other variations 80 mol. %, or 85 mol. %, or 90 mol. %, or 91 mol. %, or 92 mol. %, or 93 mol. %, or 94 mol. %, or 95 mol. %) in the starting mixture, said amount being expressed as the amount of 1,4-bis(4-phenoxybenzoyl)benzene relative to the initial amount of terephthaloyl chloride reactant which was introduced.

Preferably, the 1,4-bis(4-phenoxybenzoyl)benzene-Lewis acid complex is dissolved in the reaction solvent at a 1,4-bis(4-phenoxybenzoyl)benzene weight concentration which is higher by at least 5%, (or in other variations by at least 10%, or 15%, or 20%, or 25%, or 30%, or 35%, or 40%) than the saturation limit of the 1,4-bis(4-phenoxybenzoyl)benzene-Lewis acid complex, during part of the reaction step, and for instance during at least 5 minutes, or at least 10 minutes, or at least 15 minutes, or at least 20 minutes, or at least 30 minutes, or at least 40 minutes, or at least 1 hour.

Preferably, the 1,4-bis(4-phenoxybenzoyl)benzene-Lewis acid complex is dissolved in the reaction solvent (without precipitation) at a 1,4-bis(4-phenoxybenzoyl)benzene concentration of more than 5 wt. %, or more than 10 wt. %, or more than 15 wt. %, or more than 20 wt. %, or more than 25 wt. %, or more than 30 wt. %, or more than 35 wt. %, or more than 40 wt. %, or more than 50 wt. %, during part of the reaction step.

In order to maintain the concentration of dissolved 1,4-bis(4-phenoxybenzoyl)benzene-Lewis acid complex in the reaction solvent above the saturation limit during the reaction, nucleation of the precipitate should be prevented or at least delayed. Several measures can be taken in this respect, in a non-limiting manner, in addition to the quality of the starting materials (already addressed above).

First, the internal walls of the reactor (which are in contact with the starting mixture) should have a low surface roughness. Preferably the surface roughness Ra (as defined in ISO 4287) of the walls should be less than 2 μm, or less than 1 μm, or less than 0.8 μm, or less than 0.5 μm, or less than 0.2 μm.

Similarly, it is preferable that all equipment surfaces in contact with the starting mixture during the reaction step, such as the surfaces of an impeller (if any) or the internal surfaces of a recirculation loop, should also have a rugosity of less than 2 μm, or less than 1 μm, or less than 0.8 μm, or less than 0.5 μm, or less than 0.2 μm.

Second, the method may comprise a preliminary step of washing the reactor, in order to eliminate all solid residues, such as dust particles or residual product particles from a previous reaction, before providing the starting mixture in the reactor. As an example, this can be achieved by spraying or blasting a liquid or a solid or a suspension on reactor wall, preferably the reaction solvent, or by filling the reactor with a liquid or a suspension under agitation, or by any mechanical action.

Third, the method may comprise a step of eliminating solid particles from the starting mixture, either before the start of the reaction step or during the reaction step, such as by filtration (including, e.g., ultrafiltration).

Fourth, the conditions (in particular intensity) of agitation during the reaction step may be selected in such a manner that the average shear stress (calculated as the product $K_{mo} \times N$ where $K_{mo}$ is the Metzner-Otto constant for the impellers used and N is the rotation frequency) for the starting mixture remains below $100 \text{ s}^{-1}$, preferably below $50 \text{ s}^{-1}$, more preferably below $25 \text{ s}^{-1}$, even more preferably below $20 \text{ s}^{-1}$ during at least part of the reaction step, and more particularly during the part of the reaction step when the concentration of the dissolved 1,4-bis(4-phenoxybenzoyl)benzene-Lewis acid complex in the reaction solvent is above the saturation limit (such as during the last 5%, or the last 10%, or the last 15%, or the last 20%, or the last 25%, or the last 30%, or the last 35%, or the last 40%, or the last 45%, or the last 50% of the reaction step, relative to the overall duration of the reaction step).

Once the reaction is completed to the desired degree, the mixture becomes designated as a product mixture.

The product mixture comprises 1,4-bis(4-phenoxybenzoyl)benzene-Lewis acid complex. The 1,4-bis(4-phenoxybenzoyl)benzene-Lewis acid complex is, at least partly, present as a precipitate, that is to say as a solid in the product mixture, but can also to some extent be solubilized in the reaction solvent. In some embodiments, the 1,4-bis(4-phenoxybenzoyl)benzene-Lewis acid complex precipitate has a volumetric mass density between $1.34 \text{ kg/m}^3$ and $2.40 \text{ kg/m}^3$, measured by a pycnometer at 23° C. The higher the volumetric mass density of 1,4-bis(4-phenoxybenzoyl)benzene-Lewis acid complex precipitate is, the easier it is to separate it from liquid by solid/liquid extraction. In particular, the 1,4-bis(4-phenoxybenzoyl)benzene-Lewis acid complex precipitate has often a volumetric mass density between $1.50 \text{ kg/m}^3$ and $2.20 \text{ kg/m}^3$. In particular, the volumetric mass density of 1,4-bis(4-phenoxybenzoyl)benzene-Lewis acid complex precipitate can be between $1.60 \text{ kg/m}^3$ and $2.00 \text{ kg/m}^3$.

The method of measurement of volumetric mass densities using a pycnometer is well known by the skilled person and has for example been described in "Materials Handbook: A Concise Desktop Reference; 3rd edition. Francois Cardarelli. chapter 1.1.7". For instance, heptane can be the liquid used for such a measurement.

According to some embodiments, preferably at least 50 wt. % of the 1,4-bis(4-phenoxybenzoyl)benzene-Lewis acid complex is in the form of a precipitate in the product mixture, preferably more than 50 wt. %, preferably at least 70 wt. %, preferably at least 90 wt. %, preferably at least 95 wt. % and preferably at least 99 wt. %.

In order to foster the 1,4-bis(4-phenoxybenzoyl)benzene-Lewis acid complex precipitation, the product mixture can be submitted to different additional treatments which aim at reducing the solubility of 1,4-bis(4-phenoxybenzoyl)benzene-Lewis acid complex and/or prevent any supersaturation phenomenon.

In particular, the product mixture can be cooled down. Preferably, the cooling rate may for instance be from 1 to 10° C./h, 10 to 20° C./h, or from 20 to 40° C./h, or from 40 to 60° C./h, or from 60 to 90° C./h, or from 90 to 120° C./h, or from 120 to 180° C./h, or higher than 180° C./h.

Alternatively, or in addition, the product mixture can be submitted to shear stress.

Alternatively, or in addition, the product mixture can be subject to the elimination by distillation of part of the reaction solvent.

Alternatively, or in addition, the product mixture can be subject to the addition of a compound in solid form acting as a seed for crystallization. Preferably, this compound in solid form can be 1,4-bis(4-phenoxybenzoyl)benzene. This compound in solid form can also be any compound which is soluble in the decomplexing solvent used for the subsequent step of dissociating the 1,4-bis(4-phenoxybenzoyl)benzene-Lewis acid complex in 1,4-bis(4-phenoxybenzoyl)benzene and Lewis acid.

A solid/liquid separation is thereafter carried out on the product mixture to separate a cake from a liquid phase. The cake contains the solid matter of the product mixture and therefore comprises the 1,4-bis(4-phenoxybenzoyl)benzene-Lewis acid complex precipitate. The cake mostly consists of solid matter but can still contain some liquid fraction and hence can have the consistence of a very pasty solid or a very viscous slurry.

The liquid phase consists of reaction solvent, unreacted chemicals, if any, and soluble impurities such as xanthydrol moiety-containing molecules.

Therefore, it is particularly advantageous to obtain a cake with a high solid content so that most of soluble impurities in the reaction solvent can be eliminated with the liquid phase.

Advantageously, the cake has a solid content of at least 40 wt. % (weight percent). Preferably, the cake has a solid content of at least 50 wt. %, or at least 60 wt. %, or at least 70 wt. %, or at least 75 wt. %, or at least 80 wt. %, or at least 85 wt. %, or at least 90 wt. %, or at least 95 wt. %. More preferably the cake has a solid content of about 100 wt. %.

The liquid content of the cake can be determined by assaying with gas chromatography (GC), high-performance liquid chromatography (HPLC), or nuclear magnetic resonance (NMR) the amount of liquid(s) impregnating the solid matter of the cake. In this case, the solid content (in wt. %) is therefore equal to: 100%-wt. % of liquid(s).

Another way, slightly less accurate, to measure the solid content is to dry a sample of the cake until a constant mass is reached. The man skilled in the art commonly knows how to adapt the time and temperature of heating, possibly under reduced pressure in function of the nature of the reaction solvent used. The solid content is the mass obtained after drying divided by the mass of the sample before drying.

The temperature when carrying out the solid/liquid separation of the product mixture is advantageously adapted so that as little as possible 1,4-bis(4-phenoxybenzoyl)benzene-Lewis acid complex is solubilized in the reaction solvent.

In particular, in some embodiments the temperature when carrying out the solid/liquid separation of the product mixture does not exceed 79° C. Preferably, the temperature when carrying out the solid/liquid separation of the product mixture does not exceed 60° C. More preferably, the temperature when carrying out the solid/liquid separation of the product mixture does not exceed 30° C.

The solid/liquid separation can be carried out in one or more successive steps, each step being chosen from the group consisting of: centrifugal filtration, sedimentation, centrifugal decanting, filtration under vacuum, filtration under pressure and gravity filtration.

In some particular embodiments, the solid/liquid separation may comprise one step performed by centrifugal filtration, in a centrifugal filtration device. It has been found that centrifugal filtration is particularly efficient and quick for performing the desired solid/liquid separation.

The centrifugal filtration device may in particular have a horizontal axis or a vertical axis.

Centrifugal filtration is preferably performed at an acceleration rate of from 2 to 1500 g, more preferably of from 5 to 1000 g, and most preferably of from 10 to 800 g.

Different acceleration values or ranges may be used during successive phases of centrifugal filtration, such as a loading phase, a washing phase and/or a dewatering phase. By way of example, a low acceleration may be applied first, followed by higher acceleration. The dry solid matter content of the cake obtained at the end of the filtration by centrifugal filtration is preferably from 65 wt. % to 100 wt. %, more preferably from 70 wt. % to 98 wt. %, even more preferably from 80 to 97 wt. %, and most preferably from 90 to 96 wt. %.

The cake is thereafter put into contact with a decomplexing solvent, the decomplexing solvent being a protic solvent. This enables to dissociate the 1,4-bis(4-phenoxybenzoyl)benzene-Lewis acid complex into 1,4-bis(4-phenoxybenzoyl)benzene and into a derivative of Lewis acid which is mostly solubilized in the decomplexing solvent under a form depending on the nature of the decomplexing solvent. For example, the derivative of Lewis acid can be under the form of a ionic salt, metal hydroxides and their counter-ions, metal alkoxides and their counter-ions or any other compound(s) resulting from the reaction of the Lewis acid with the decomplexing solvent.

The relative weight ratio of cake and decomplexing solvent put in contact is preferably from 20 to 0.5, most preferably from 10 to 1, more preferably from 5 to 3.

The decomplexing solvent can be an organic solvent, such as methanol, acetic acid, formic acid, ethanol, isopropanol, and benzyl alcohol. Methanol is preferred as an organic solvent.

Alternatively, the decomplexing solvent can be an aqueous solution.

Mixtures of the above solvents can also be used, such as an aqueous-organic solvent, e.g., an aqueous solution mixed with methanol.

Using an aqueous solution as the decomplexing solvent for performing the dissociation of the 1,4-bis(4-phenoxybenzoyl)benzene-Lewis acid complex is especially advantageous for two reasons. Firstly, an aqueous solution has a relatively large heat capacity. This makes it possible to achieve a better dissipation of the heat generated as a result of the highly exothermic dissociation of the 1,4-bis(4-phenoxybenzoyl)benzene-Lewis acid complex. Less vapor may thus be generated than if, e.g., methanol is used. More generally, the safety of the process is improved. Secondly, the Lewis acid derivative can be recovered from the aqueous solution. This aqueous stream can be more easily directly recycled and reused than, e.g., a methanol stream. For instance, when the Lewis acid used for the reaction is aluminum trichloride, the aqueous effluent of aluminum trichloride can be directly used as a flocculation agent in wastewater treatment. Conversely, aluminum trichloride in methanol is a waste effluent which should be disposed of.

The aqueous solution can be simply water.

In some embodiments, the aqueous solution can be an acidic solution, such as a solution of hydrochloric acid, phosphoric acid, sulfuric acid, nitric acid, an organic acid such as formic acid and any combination of these. In particular, the aqueous solution can be a solution of hydrochloric acid. Preferably, the aqueous solution has a pH of no more than 6, or no more than 5, or not more than 4, or no more than 3, or no more than 2, or no more than 1, or no more than 0. Preferably, the aqueous has a pH between 1 and 2.

In particular, the decomplexing solvent can be an aqueous solution containing hydrochloric at a concentration corresponding to such pH values.

For these pH values, when the Lewis acid is for instance aluminum trichloride, the aluminum is mostly in a soluble $Al^{3+}$ form, soluble in the aqueous solution, and consequently can be efficiently separated from a 4-bis(4-phenoxybenzoyl)benzene.

Alternatively, in other embodiments, the aqueous solution can be a basic solution, such as a solution of caustic soda, potassium hydroxide, calcium hydroxide, sodium carbonate, calcium carbonate, magnesium carbonate, potassium carbonate, ammoniac, or their mixtures. In these embodiments, the aqueous solution has preferably a pH of more than 9, or more than 10, or more than 11, or more than 12, or more than 13, or more than 14. Preferably, the decomplexing solvent has a pH between 12 and 14.

In particular, the decomplexing solvent can be an aqueous solution containing NaOH at a concentration corresponding to such pH values.

For these pH values, when the Lewis acid is for instance aluminum trichloride, the aluminum is predominantly in a soluble $[Al(OH)_4]^-$ form, soluble in the aqueous solution, and consequently can be efficiently separated from 4-bis(4-phenoxybenzoyl)benzene.

The dissociation of the 1,4-bis(4-phenoxybenzoyl)benzene-Lewis acid complex into 1,4-bis(4-phenoxybenzoyl)benzene may be more efficient when an acidic solution is used.

Once the entirety of the cake and of the aqueous solution have been put in contact, the mixture of both can be maintained, preferably with agitation, for a period of time of, e.g., from 1 to 600 minutes, preferably from 5 to 300 minutes, more preferably from 20 to 90 minutes.

Temperature may optionally be controlled at this stage, and for instance the mixture may be cooled. Temperature control and cooling devices as already mentioned above may be used to this end.

In an alternative variation, the temperature is not controlled at this stage, and it thus rises, possibly up to the boiling point of one or more of the solvents (including, e.g., water) present in the mixture. The steam thus generated can be collected and then treated and/or recycled or disposed of.

The mixture can optionally cool down (or be actively cooled down) after this exothermic surge.

In the embodiment according to which the cake obtained at the previous stage had a solid content of about 100 wt. %, only one phase is obtained: the Lewis acid is solubilized in the decomplexing solvent under a form depending on the nature of the decomplexing solvent and 1,4-bis(4-phenoxybenzoyl)benzene is mostly in the form of a precipitate in the decomplexing solvent. In these embodiments, preferably at least 50 wt. % of the 1,4-bis(4-phenoxybenzoyl)benzene is in the form of a precipitate in the decomplexing solvent, preferably more than 50 wt. %, preferably at least 70 wt. %, preferably at least 90 wt. %, preferably at least 95 wt. % and preferably at least 99 wt. %.

In the embodiments according to which the cake obtained at the previous stage still contains a liquid fraction, for example in the case the liquid fraction is over 5 wt. %, or over 10 wt. %, or over 20 wt. %, or over 30 wt. %, a first phase with the decomplexing solvent containing mostly the solubilized Lewis acid derivative under a form depending on the nature of the decomplexing solvent and a second phase with the reaction solvent containing mostly the 1,4-bis(4-phenoxybenzoyl)benzene) are obtained.

In particular, at least 50 wt. % of the Lewis acid is present in the first phase, preferably more than 50 wt. %, preferably at least 70 wt. %, preferably at least 90 wt. %, preferably at least 95 wt. %, preferably 99 wt. %. In addition at least 50 wt. % of the 1,4-bis(4-phenoxybenzoyl)benzene is present in the second phase, preferably more than 50 wt. %, preferably at least 70 wt. %, preferably at least 90 wt. %, preferably at least 95 wt. %, preferably 99 wt. %

The 1,4-bis(4-phenoxybenzoyl)benzene in the second phase is mostly in the form of a precipitate. The second phase can have the consistence of a very pasty solid or a very viscous slurry. In particular, preferably at least 50 wt. % of the 1,4-bis(4-phenoxybenzoyl)benzene is in the form of a precipitate in the second phase, preferably more than 50 wt. %, preferably at least 70 wt. %, preferably at least 90 wt. %, preferably at least 95 wt. % and preferably at least 99 wt. %.

If an aqueous solution is used as the decomplexing solvent, the first phase is an aqueous phase and the second phase is an organic phase. 1,4-bis(4-phenoxybenzoyl)benzene is mostly present in the organic phase in the form of a precipitate while the derivative of Lewis acid is mostly present in the aqueous phase, solubilized under a form depending on the nature of the aqueous solution.

The first phase and second phase may be separated so as to be recovered separately, preferably by decantation. Accordingly, an upper phase may be transferred out from the top of the decantation device and/or a lower phase may be transferred from the bottom of the decantation device, to a second equipment. These transfers may be driven by one or more pumps, by gravity or by a difference in pressure.

The 1,4-bis(4-phenoxybenzoyl)benzene precipitate can be recovered by any means of solid/liquid separation, as previously mentioned in the specification. The solid/liquid separation can be carried out in one or more successive steps, each step being chosen from the group consisting of: centrifugal filtration, sedimentation, centrifugal decanting, filtration under vacuum, filtration under pressure and gravity filtration. In particular, the solid/liquid separation to recover 1,4-bis(4-phenoxybenzoyl)benzene can be carried out by one step of filtration.

If necessary, the recovered 1,4-bis(4-phenoxybenzoyl)benzene can be further purified by methods well-known by the skilled person such as being submitted to washing step(s), and/or recrystallization step(s) and/or distillation step(s) to eliminate or reduce the amount of remaining impurities, such as in particular, the 4-(4-phenoxybenzoyl)benzoic acid and 4-(4-phenoxybenzoyl)benzoic acid ester impurities. In particular, the product can be washed, preferably by a protic solvent such as methanol, and filtrated again, once or several times. Washing can be performed for example by re-slurrying the product in the solvent. The product can also undergo a step to modify the particles size and the morphology of the particles.

The purity of 1,4-bis(4-phenoxybenzoyl)benzene may be determined by a number of methods, including nuclear magnetic resonance (NMR), differential scanning calorimetry (DSC), gas chromatography (GC) or high-performance liquid chromatography (HPLC). Preferably, said purity is determined by HPLC.

The 1,4-bis(4-phenoxybenzoyl)benzene obtained according to embodiments of the invention can subsequently be used to perform a polymerization reaction so as to make a polyaryletherketone polymer (PAEK). In particular, the 1,4-bis(4-phenoxybenzoyl)benzene obtained according to embodiments of the invention can subsequently be used to perform a polymerization reaction so as to make a polyether ketone ketone polymer (PEKK).

In order to make the PAEK polymer, 1,4-bis(4-phenoxybenzoyl)benzene is reacted with at least one difunctional aromatic acyl chloride.

The difunctional aromatic acyl chloride may be chosen among the list consisting of: terephthaloyl chloride, isophthaloyl chloride, phthaloyl chloride, phosgene, adipoyl dichloride, tetrabromophthaloyl chloride, and compounds of the following formula:

wherein:
a is an integer between 0 to 3;
V is chosen among: —O—, —S—, —N=N—, —(CF$_2$)$_q$—, —(CH$_2$)$_q$—, or —C((CH$_3$)$_2$)—; and
Z is chosen among —C(O)—, —SO$_2$—, —C(O)—C$_6$H$_4$—C(O)—, —O—(CF$_2$)$_q$—O—, —S—, —N=N—, —(CF$_2$)$_q$—, —(CH$_2$)$_q$—, or C—(CH$_3$)$_2$—,
wherein q is an integer between 1 to 20; and
mixtures thereof.

In the embodiment in which the PAEK is PEKK, the difunctional aromatic acyl chloride can be a mixture of phthaloyl chloride, terephthaloyl chloride, and isophthaloyl chloride. Preferably, the difunctional aromatic acyl chloride is a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof. Ortho-dichlorobenzene is the most preferred solvent.

The reaction is preferably implemented in the presence of a Lewis acid as a catalyst.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The polymerization can be implemented in the same reactor as the one used for the production of 1,4-bis(4-phenoxybenzoyl)benzene. But more preferably it is implemented in one or more other reactors.

The polymerization can be carried out at a temperature ranging from, e.g., 20 to 120° C.

The method of making the PAEK polymer, and in particular PEKK, advantageously also comprises one or more steps for purifying the PAEK polymer, such as steps of:
  mixing the mixture containing the PAEK polymer with a protic solvent so as to provide a PAEK slurry;
  separating the PAEK polymer from the PAEK slurry, preferably by filtration and washing.

The protic solvent used to make the PAEK slurry may be, e.g., methanol.

The PAEK polymer can then be recovered from the PAEK slurry by filtration. If necessary, the polymer can be washed, preferably by a protic solvent such as methanol, and filtrated again, once or several times. Washing can be performed for example by re-slurrying the polymer in the solvent.

EXPERIMENTS

The following illustrates certain embodiments of the invention without limiting it.

Saturation Limit of the 1,4-bis(4-phenoxybenzoyl)benzene-Lewis Acid Complex

Figure 2:
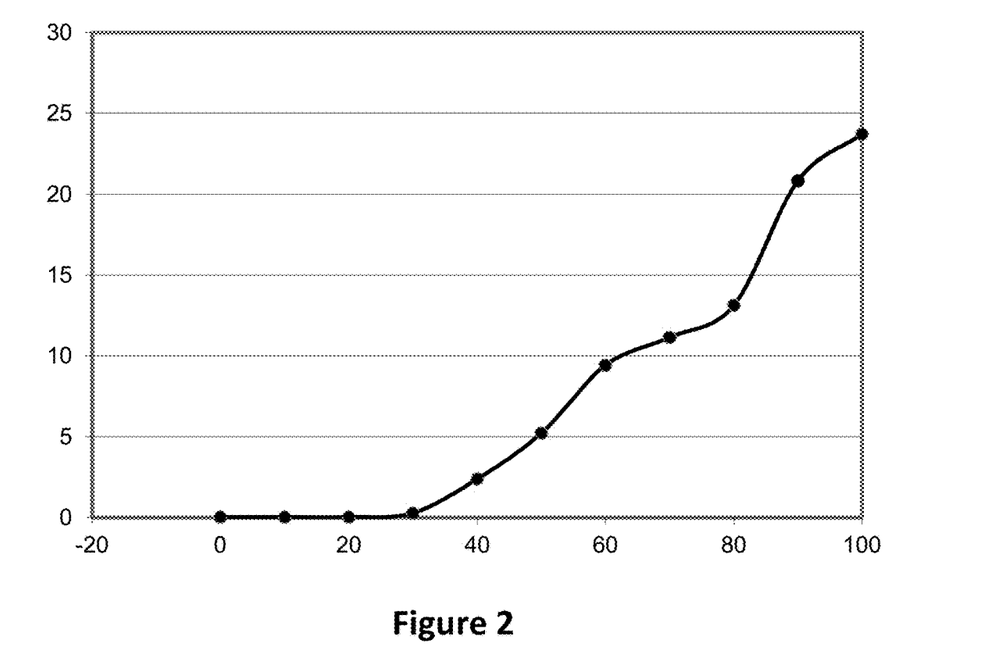
FIG. 2 shows a graph of the saturation limit of the 1,4-bis(4-phenoxybenzoyl)benzene-aluminum trichloride complex in orthodichlorobenzene, as a function of temperature.

FIG. 2 is a graph representing the saturation limit of the 1,4-bis(4-phenoxybenzoyl)benzene-Lewis acid complex in ortho-dichlorobenzene, as a function of temperature. Temperature in ° C. is provided on the X axis. The weight concentration in % of 1,4-bis(4-phenoxybenzoyl)benzene in ortho-dichlorobenzene at saturation is provided in the Y axis. The Lewis acid-to-1,4-bis(4-phenoxybenzoyl)benzene molar ratio is 4.05. The Lewis acid is aluminum trichloride.

FIG. 2 highlights the importance of carrying out the solid/liquid separation of the product mixture to obtain a cake comprising the 1,4-bis(4-phenoxybenzoyl)benzene-Lewis acid complex precipitate at a temperature lower than 79° C., preferably at a temperature lower than 60° C., even more preferably at a temperature lower than 30° C. As a matter of fact, at 30° C. the 1,4-bis(4-phenoxybenzoyl)benzene-Lewis acid complex has a solubility close to zero in ortho-dichlorobenzene.

Example 1

In a 2 L reactor equipped with a mechanical stirrer, with a nitrogen inlet and outlet going to a scrubber system, 403 g of ortho-dichlorobenzene was introduced, 29 g of terephthaloyl chloride and 71 g of diphenyl ether. After full solubilization, the mixture was heated to 29° C. While keeping this temperature at 29° C., 61 g of $AlCl_3$ was slowly added to the reaction mixture. After completion of $AlCl_3$ addition, the mixture was kept agitated at 25° C. during 3 h to finish the reaction. The suspension obtained was then poured at 25° C. in a pore 3 sintered glass filter under vacuum. The cake obtained on the filter contains about 55 wt. % of remaining liquid (ratio of the weight of liquid contained in the cake divided by the total weight of the cake) as measured by NMR. It was then placed in a beaker containing an aqueous solution of HCl at 3 wt. % and agitated with a magnetic stirrer. After removal of the aqueous aluminic phase, EKKE was obtained with a yield of 82%.

It can be shown that all of the xanthydrol moiety-containing molecules are in the liquid phase of the suspension. Consequently, the part remaining in the cake obtained after solid/liquid separation comes only from the liquid fraction impregnating the solid particles of the 1,4-bis(4-phenoxybenzoyl)benzene-Lewis acid complex precipitate. Therefore, the less liquid fraction is left in the cake, the higher the purity of its non-solvent fraction, as shown in table 1.

TABLE 1

| Liquid fraction of the cake (wt. %) | xanthydrol moiety-containing molecule in the cake (wt. %) | % purity of the EKKE |
| --- | --- | --- |
| 75% | 2.0% | 98.0% |
| 60% | 1.0% | 99.0% |
| 50% | 0.7% | 99.3% |
| 25% | 0.2% | 99.8% |

Embodiments

1. A method for manufacturing 1,4-bis(4-phenoxybenzoyl)benzene, comprising:
    reacting terephthaloyl chloride with diphenyl ether in the presence of a Lewis acid, so as to obtain a product mixture comprising 1,4-bis(4-phenoxybenzoyl)benzene-Lewis acid complex, wherein the 1,4-bis(4-phenoxybenzoyl)benzene-Lewis acid complex is, at least partly, in the form of a precipitate;
    carrying out a solid/liquid separation of the product mixture to obtain a cake comprising the 1,4-bis(4-phenoxybenzoyl)benzene-Lewis acid complex precipitate;
    putting the cake in contact with a decomplexing solvent, wherein the decomplexing solvent is a protic solvent, so as to dissociate the 1,4-bis(4-phenoxybenzoyl)benzene-Lewis acid complex into 1,4-bis(4-phenoxybenzoyl)benzene; and,
    recovering the 1,4-bis(4-phenoxybenzoyl)benzene.

2. The method of embodiment 1, wherein reacting terephthaloyl chloride with diphenyl ether in the presence of a Lewis acid is carried out in a reaction solvent, wherein the reaction solvent is separate from the terephthaloyl chloride, the diphenyl ether, and the Lewis acid;
    preferably, wherein the reaction solvent is non-protic;
    more preferably wherein the reaction solvent is selected from the group consisting of: methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1-dichloroethane, 1,1,2,2-tetrachloroethane, tetrachloroethylene, dichloromethane, nitrobenzene and mixtures thereof; and, even more preferably, wherein the reaction solvent is ortho-dichlorobenzene.

3. The method of embodiment 1 or embodiment 2, wherein the 1,4-bis(4-phenoxybenzoyl)benzene-Lewis acid complex precipitate has a density between 1.34 and 2.40, measured by a pycnometer at 23° C.

4. The method of any one of embodiments 1 to 3, wherein the cake has a solid content of at least 40 wt. %;
    preferably, wherein the cake has a solid content of at least 50 wt. %, or at least 60 wt. %, or at least 70 wt. %, or at least 75 wt. %, or at least 80 wt. %, or at least 85 wt. %, or at least 90 wt. %, or at least 95 wt. %; and,
    more preferably wherein the cake has a solid content of about 100 wt. %.

5. The method of any one of embodiments 1 to 4, wherein the decomplexing solvent is chosen from the group consisting of: methanol, acetic acid, formic acid, ethanol, isopropanol, benzyl alcohol, aqueous solutions and mixtures thereof.

6. The method of embodiment 5, wherein the decomplexing solvent is an aqueous solution.

7. The method of any one of embodiments 1 to 6, wherein the decomplexing solvent has a pH of no more than 6, or no more than 5, or not more than 4, or no more than 3, or no more than 2, or no more than 1, or no more than 0;
    preferably, wherein the decomplexing solvent has a pH between 1 and 2.

8. The method of any one of embodiments 1 to 6, wherein the decomplexing solvent has a pH of more than 9, or more than 10, or more than 11, or more than 12, or more than 13;
    preferably wherein the decomplexing solvent has a pH between 12 and 14.

9. The method of any one of embodiments 6 or 7, wherein the aqueous solution is an aqueous solution of HCl.

10. The method of any one of embodiments 1 to 9, wherein the temperature when carrying out the solid/liquid separation of the product mixture does not exceed 79° C.;
preferably wherein the temperature when carrying out the solid/liquid separation of the product mixture does not exceed 60° C.; and,
more preferably wherein the temperature when carrying out the solid/liquid separation of the product mixture does not exceed 30° C.

11. The method of any one of embodiments 1 to 10, wherein the solid/liquid separation is carried out in one or more successive steps, each step being chosen from the group consisting of: centrifugal filtration, sedimentation, centrifugal decanting, filtration under vacuum, filtration under pressure and gravity filtration.

12. The method of any one of embodiments 1 to 11, wherein the Lewis acid is selected from the group consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride;
preferably, wherein the Lewis acid is selected from the group consisting of: aluminum trichloride, boron trichloride, aluminum tribromide, titanium tetrachloride, antimony pentachloride, ferric chloride, gallium trichloride, and molybdenum pentachloride; and,
more preferably, wherein the Lewis acid is aluminum trichloride.

13. The method of any one of embodiments 1 to 12, wherein before carrying out a solid/liquid separation of the product mixture, the product mixture is cooled down and/or submitted to shear stress and/or subject to the elimination by distillation of part of the reaction solvent, and/or subject to the addition of a compound in solid form acting as a seed in order to foster the 1,4-bis(4-phenoxybenzoyl)benzene-Lewis acid complex precipitation.

14. The method of any one of embodiments 1 to 13, wherein reacting terephthaloyl chloride with diphenyl ether in the presence of a Lewis acid is carried out, at least partly, at a temperature greater than 5° C.

15. The method of any one of embodiments 1 to 14, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU.

16. The method of any one of embodiments 2 to 15, wherein the 1,4-bis(4-phenoxybenzoyl)benzene-Lewis acid complex is dissolved in the reaction solvent at a 1,4-bis(4-phenoxybenzoyl)benzene weight concentration in the solvent which is higher than the saturation limit of the 1,4-bis(4-phenoxybenzoyl)benzene-Lewis acid complex during at least part of the reaction of the terephthaloyl chloride with the diphenyl ether.

17. A method of making a polyaryletherketone polymer, comprising:
manufacturing 1,4-bis(4-phenoxybenzoyl)benzene according to the method of any one of embodiments 1 to 16; and,
reacting the 1,4-bis(4-phenoxybenzoyl)benzene with at least one difunctional aromatic acyl chloride.

The invention claimed is:

1. A method for manufacturing 1,4-bis(4-phenoxybenzoyl)benzene, comprising:
reacting terephthaloyl chloride with diphenyl ether in the presence of a Lewis acid, so as to obtain a product mixture comprising 1,4-bis(4-phenoxybenzoyl)benzene-Lewis acid complex, wherein the 1,4-bis(4-phenoxybenzoyl)benzene-Lewis acid complex is, at least partly, in the form of a precipitate;
carrying out a solid/liquid separation of the product mixture to obtain a cake comprising the 1,4-bis(4-phenoxybenzoyl)benzene-Lewis acid complex precipitate;
putting the cake in contact with a decomplexing solvent, wherein the decomplexing solvent is a protic solvent, so as to dissociate the 1,4-bis(4-phenoxybenzoyl)benzene-Lewis acid complex into 1,4-bis(4-phenoxybenzoyl)benzene; and,
recovering the 1,4-bis(4-phenoxybenzoyl)benzene.

2. The method of claim 1, wherein reacting terephthaloyl chloride with diphenyl ether in the presence of a Lewis acid is carried out in a reaction solvent, wherein the reaction solvent is separate from the terephthaloyl chloride, the diphenyl ether, and the Lewis acid.

3. The method of claim 1, wherein the 1,4-bis(4-phenoxybenzoyl)benzene-Lewis acid complex precipitate has a density between 1.34 and 2.40, measured by a pycnometer at 23° C.

4. The method of claim 1, wherein the cake has a solid content of at least 40 wt. %.

5. The method of claim 1, wherein the decomplexing solvent is chosen from the group consisting of: methanol, acetic acid, formic acid, ethanol, isopropanol, benzyl alcohol, aqueous solutions and mixtures thereof.

6. The method of claim 5, wherein the decomplexing solvent is an aqueous solution.

7. The method of claim 1, wherein the decomplexing solvent has a pH of no more than 6.

8. The method of claim 1, wherein the decomplexing solvent has a pH of more than 9.

9. The method of claim 6, wherein the aqueous solution is an aqueous solution of HCl.

10. The method of claim 1, wherein the temperature when carrying out the solid/liquid separation of the product mixture does not exceed 79° C.

11. The method of claim 1 wherein the solid/liquid separation is carried out in one or more successive steps, each step being chosen from the group consisting of: centrifugal filtration, sedimentation, centrifugal decanting, filtration under vacuum, filtration under pressure and gravity filtration.

12. The method of claim 1, wherein the Lewis acid is selected from the group consisting of: aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride.

13. The method of claim 1, wherein before carrying out a solid/liquid separation of the product mixture, the product mixture is cooled down and/or submitted to shear stress and/or subject to the elimination by distillation of part of the reaction solvent, and/or subject to the addition of a compound in solid form acting as a seed in order to foster the 1,4-bis(4-phenoxybenzoyl)benzene-Lewis acid complex precipitation.

14. The method of claim 1, wherein reacting terephthaloyl chloride with diphenyl ether in the presence of a Lewis acid is carried out, at least partly, at a temperature greater than 5° C.

15. The method of claim 1, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU.

16. The method of claim 2, wherein the 1,4-bis(4-phenoxybenzoyl)benzene-Lewis acid complex is dissolved in the reaction solvent at a 1,4-bis(4-phenoxybenzoyl)benzene weight concentration in the solvent which is higher than the saturation limit of the 1,4-bis(4-phenoxybenzoyl)benzene-Lewis acid complex during at least part of the reaction of the terephthaloyl chloride with the diphenyl ether.

17. A method of making a polyaryletherketone polymer, comprising:
- manufacturing 1,4-bis(4-phenoxybenzoyl)benzene according to the method of claim 1; and,
- reacting the 1,4-bis(4-phenoxybenzoyl)benzene with at least one difunctional aromatic acyl chloride.

* * * * *